United States Patent [19]

Grega née Tóth et al.

[11] Patent Number: 4,623,383
[45] Date of Patent: Nov. 18, 1986

[54] NOVEL N- AND OPTIONALLY N-SUBSTITUTED (N-DICHLORO-ACETYL)GLYCINE AMIDES WITH AN ANTIDOTE ACTION

[75] Inventors: Erzsébet Grega née Tóth; József Nagy; Gyula Tarpai; Ernö Lörik; István Tóth; Károly Pásztor; Zsuzsanna Bártfai née Harsányi, all of Miskolc; Ilona Béres, Boldva; László Tasi, Miskolc; Eszter Urszin née Simon, Sajóbábony; Zsolt Dombay; Judit Bajusz née Oláh, both of Miskolc; Károly Balogh, Miskolc, all of Hungary

[73] Assignee: Eszakmagyarorszagi Vegyimuvek, Sajobabony, Hungary

[21] Appl. No.: 633,382

[22] Filed: Jul. 23, 1984

[30] Foreign Application Priority Data

Jul. 21, 1983 [HU] Hungary ............................. 2565/83

[51] Int. Cl.$^4$ ..................... C07C 103/50; A01N 43/46; A01N 47/12; A01N 37/22
[52] U.S. Cl. .......................................... 71/100; 71/88; 71/92; 71/118; 564/155; 564/159; 564/152; 540/607
[58] Field of Search ................. 260/239 BF; 564/155, 564/152, 159; 71/100, 118, 88, 92

[56] References Cited

U.S. PATENT DOCUMENTS

| | | | |
|---|---|---|---|
| 3,803,181 | 4/1974 | Shigemasa et al. | 260/372 |
| 4,021,224 | 5/1977 | Pallos et al. | 564/155 X |
| 4,231,786 | 11/1980 | Czajkowski et al. | 71/100 |
| 4,249,933 | 2/1981 | Hansen et al. | 71/100 |
| 4,509,974 | 4/1985 | Gray et al. | 71/100 |

FOREIGN PATENT DOCUMENTS

| | | | |
|---|---|---|---|
| 0527481 | 7/1956 | Canada | 564/155 |
| 0699162 | 12/1964 | Canada | 564/155 |
| 179259 | 11/1979 | Hungary . | |

OTHER PUBLICATIONS

Vass et al., Substituted α-Aminocarboxamide Herbicides, CA:92:146457a, Hung. Teljes 17,273, 2/17/1978.

Primary Examiner—Charles F. Warren
Assistant Examiner—Carolyn S. Greason
Attorney, Agent, or Firm—Karl F. Ross; Herbert Dubno

[57] ABSTRACT

The present invention relates to novel N- and optionally N'-substituted (N-dichloroacetyl)glycine amides of the formula I with antidote action, to antidote compositions containing such compounds, to selective herbicide compositions containing these antidotes together with herbicidally active compounds and to a method for treating cultivated plants with said compositions.

11 Claims, No Drawings

NOVEL N- AND OPTIONALLY N-SUBSTITUTED (N-DICHLORO-ACETYL)GLYCINE AMIDES WITH AN ANTIDOTE ACTION

FIELD OF THE INVENTION

The present invention relates to novel N- and optionally N'-substituted (N-dichloroacetyl)glycine amides of the formula

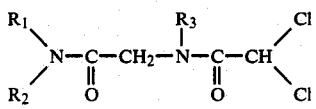

with an antidote action, to antidote compositions containing such compounds, to selective herbicide compositions containing these antidotes together with herbicidally active compounds, preferably thiolcarbamates of the formula

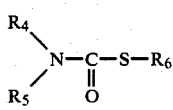

or chloroacetanilides of the formula

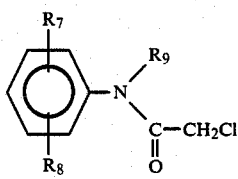

and to a method for treating cultivated plants with said compositions. The invention further relates to the preparation of the compounds of the formula I.

In the formula I
$R_1$ and $R_2$ are the same or different, and represent hydrogen, alkyl, alkenyl, cycloalkyl, unsubstituted phenyl or phenyl substituted by alkyl, dialkyl or halo or together form a hexamethylene group,
$R_3$ is alkyl or alkenyl.

The thiolcarbamate derivatives of the formula III are widely used for controlling weeds, especially monocotyledous weeds in plant cultivation. In the formula III
$R_4$ and $R_5$ are the same or different, and represent alkyl, cycloalkyl or together form a hexamethylene group,
$R_6$ stands for alkyl.

BACKGROUND OF THE INVENTION

The most widely used thiolcarbamate derivatives are the N-N-diisobutyl-S-ethyl thiolcarbamate (Butilate), the N,N-di(n-propyl)-S-ethyl thiolcarbamate (EPTC), the N,N-di(n-propyl)-S-(n-propyl)thiolcarbamate (Vernolate), the N,N-diethyl-S-ethyl thiolcarbamate (Ethiolate), the N-ethyl-N-butyl-S-ethyl thiolcarbamate (Pebulat), the N-ethyl-N-cyclohexyl-S-ethyl thiolcarbamate (Cikloat) and N,N-hexamethylene-S-ethyl thiolcarbamate. (Molinat).

Similarly, the chloroacetanilides of the formula IV are also widely used. In the formula IV
$R_7$ and $R_8$ are the same or different and represent an alkyl group,
$R_9$ stands for alkyl, alkenyl, alkoxyalkyl or pyrazolylalkyl.

The most widely used chloroacetanilide derivatives for controlling monocotyledonous weeds are the 2-chloro-N-isopropylacetanilide (Propachlor), the 2-chloro-2',6-diethyl-N-(methoxymethyl)acetanilide (Alachlor), the 2-chloro-2'-methyl-6'-ethyl-N-(ethoxymethyl)acetanilide (Acetochlor) and the 2-chloro-2',6'-diethyl-N-(buthoxymethyl)acetanilide (Butachlor).

But both types of these two active ingredients have the disadvantage that their effective amount for controlling monocotyledonous weeds also damages the cultivated plant to be protected, that is, they are phytotoxic, therefore these compounds have a decreased applicability. Otherwise, if they are used in such an amount which is not phytotoxic for the cultivated plant, their herbicidal activity is substantially diminished.

Some two decades ago Hoffman discovered that there are compounds as, for example, the 1,8-naphthalic acid anhydride derivatives which decrease the phytotoxic effect of these compounds, i.e. there exist compounds which counteract the damaging effect of the thiolcarbamates when applied together with the thiolcarbamates.

Since then multilateral search was conducted in order to find compounds of antidote effect and such antidote compositions are referred to in countless patent specifications.

For example, the Hungarian patent specification No. 165,736 reports on the antidote effect of compounds of dichloroacetamide type, from which the N,N-diallyl-2,2-dichloroacetamide (R-25,788) is now the most widely used in practice.

The Hungarian patent specification No. 168,977 describes oxazolidine and thiazolidine type antidotes, the Hungarian patent specification No. 170,214 refers to thiazolidine sulphoxide type antidotes, the Hungarian patent specification No. 173,755 reports on antidotes of sulphide-type, the Hungarian patent specification No. 176,867 describes oxazolidine derivatives, the Hungarian patent specification No. 179,643 reports on N-(benzoylsulphonyl)-carbamate, the Hungarian patent specification No. 180,069 refers to N-(benzoylsulphonyl)-thiolcarbamate, while the Hungarian patent specification No. 180,068 describes 2,3-dibromopropionamide derivatives as antidotes.

The Hungarian patent specifications No. 176,458 and 176,784 disclose dichloroacetamide type antidotes as well.

The Hungarian patent specification Nos. 176,669, 176,796, 178,883, 178,892, 178,985, 179,092 and 179,093 report on the antidote effect of dicarboxylic acid derivatives of different structure from the above-cited dichloroacetamide derivatives.

The great number of the patent specifications show that, in spite of the wide search, nobody has managed to find compounds which could be generally used in the protection of cultivated plants against the damaging effect of certain herbicidally active agents. This fact is also supported by the failure of the searches directed to the revelation of the mechanism of the antidote effect. Namely, the researchers do not assume a uniform attitude concerning the biochemical reactions when the antidote is added to the herbicide and the influence of the antidote compounds on the processes brought about by the herbicidal compounds in the cultivated plants. The environmental constituents (e.g. temperature, humidity and pH of the soil) exerting an influence on the plants simultaneously with the effect of the herbicides used for the treatment and the physical properties (vapour pressure, solubility in water) of the herbicidally active agents multilaterally and diversely influence the damaging effect of the herbicides.

DESCRIPTION OF THE INVENTION

In the course of our experiments directed to the decreasing of the harmful effect of herbicidally active agents of thiolcarmabate and chloroacetanilide type it has been found that the N- and optionally N'-substituted (N-dichloroacetyl)glycine amides of the formula I are able to prevent the phytotoxic effect of the above-mentioned active agents.

In the formula I $R_1$ and $R_2$ are the same or different, and represent hydrogen, alkyl, alkenyl, cycloalkyl, unsubstituted phenyl or phenyl substituted by alkyl, dialkyl or halo or together form a hexamethylene group, $R_3$ is alkyl or alkenyl.

From compounds of the formula I those are preferred in which formulae $R_1$ and $R_2$ are the same or different and represent hydrogen, alkyl containing 1 to 10 carbon atoms, alkenyl containing 5 to 6 carbon atoms, unsubstituted phenyl or phenyl substituted by alkyl containing 1 to 3 carbon atoms, dialkyl containing 1 to 3 carbon atoms in the alkyl moiety or halo, or together form a hexamethylene group, $R_3$ stands for alkyl containing 1 to 5 carbon atoms or alkenyl containing 2 to 5 carbon atoms.

In the course of our experiments it was found that the compositions containing 0.1 to 80% by weight of a compound of the formula I, optionally 20 to 90% by weight of a carrier and/or diluent and 0.5 to 20% by weight of one or more excipients are suitable for the protection of cultivated plants against the damaging effect of herbicidally active agents if these compositions are applied just before, simultaneously or after the treatment with the herbicidally active agents.

Our experiments proved that the herbicide compositions containing a compound of the formula I and a thiolcarbamate of the formula III are effective against weeds while they do not harm the cultivated plants in any sense. From compounds of the formula III those are preferred, in which formulae $R_4$ and $R_5$ are the same or different and represent alkyl of 1 to 6 carbon atoms, cycloalkyl containing 5 to 6 carbon atoms or together form a hexamethylene group, $R_6$ stands for alkyl containing 1 to 5 carbon atoms.

Our experiments also proved that herbicide compositions containing a compound of the formula I and a chloroacetanilide of general formula IV are suitable for controlling monocotyldeonous weeds without any damage of the cultivated plant.

From compounds of the formula IV those are preferred in which formulae $R_7$ and $R_8$ are the same or different and represent alkyl of 1 to 5 carbon atoms, $R_9$ stands for alkyl containing 1 to 5 carbon atoms, alkenyl containing 2 to 5 carbon atoms, alkoxyalkyl or pyrazolylakyl.

The compounds of the formula I can be prepared by reacting a compound of the formula

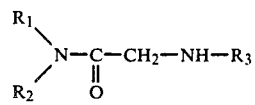

wherein the substituents are the same as defined above, with dichloroacetyl chloride, optionally in a solvent medium, in the presence of an acid-binding agent. As solvents those which are inert under the reaction conditions, preferably halogenated hydrocarbons can be used.

The hydrochloric acid formed during the reaction can be bonded by bases, preferably alkaline metal carbonates, alkaline metal bicarbonates or organic amines.

The starting materials are reacted in substantially molar equivalent amounts, but the dichloroacetyl chloride is preferably used in a small excess.

The reaction should be carried out at temperatures lower than room temperature. After the reaction is completed, the reaction mixture is allowed to warm up to room temperature; thereafter the end-product is recovered by conventional means.

SPECIFIC EXAMPLES

The preparation of some of the compounds of the formula I is shown by the following, non-limiting examples.

EXAMPLE 1

20.6 g. of N-(ethylglycine)-N'-ethyl-N'-phenyl amide are charged into a round-bottom flask of 500 ml., equipped with a thermometer, stirrer and a dropping funnel, and dissolved in 200 ml. of benzene under stirring. Thereafter a solution of 6.6 g. of sodium carbonate in 100 ml water is added. The mixture is cooled to 5° C. on ice-bath, then a solution of 16.2 g. of dichloroacetyl chloride in benzene is added dropwise while the temperature of the reaction mixture is maintained under 10° C. After the completion of the dropwise addition the mixture is stirred at room temperature for 4 hours and the benzene phase is separated from the aqueous phase. The organic phase is washed twice with water, dried over sodium sulphate, thereafter the benzene is distilled off.

.26.5 g. of N-(dichloroacetyl)-N-(ethylglycine)-N'-ethyl-N'-phenylamide are obtained. Melting point: 56°–58° C.

Yield: 80%. Purity (determined by gas chromatography): 98.2%.

Analysis: Calculated: N 8.83%; Cl: 22.39%; Found: N 8.68%; Cl: 22.16%.

EXAMPLE 2

17.0 g. of N-(allylglycine)-N',N-diethyl amide are charged into a round-bottom flask of 500 ml. equipped with a thermometer, stirrer an dropping funnel and dissolved in a mixture of 150 ml. of dichloromethane and 11.0 g. of triethyl amine. Then 16.5 g. of dichloroacetyl chloride are added dropwise to the solution under stirring and cooling with ice to 5°–10° C. After completion of the reaction the reaction mixture is washed with water, dried over sodium sulphate and the solvent is evaporated. Thus 25.2 g. of N-(dichloroacetyl)-N-(allylglycine)-N',N-diethyl amide are obtained. Melting point: 93°–95.5° C.

Yield: 90%. Purity determined by gas chromatography: 99.9%.

Analysis: Calculated: N: 9.96%; Cl: 25.26%; Found: N: 10.19%; Cl: 25.06%.

EXAMPLE 3

16.5 g. of dichloroacetyl chloride are dissolved in 150 ml. of dichloromethane under stirring in a round-bottom flask of 500 ml., equipped with a stirrer, thermometer and dropping funnel, and the solution is cooled under 10° C. on ice-bath. Thereafter a mixture of 23.4 g. of N-(n-butylglycin)-N'-ethyl-N'-phenyl amide, 11,0 g. of triethyl amine and 100 ml. of dichloromethane is added dropwise while maintaining the temperature at about 10° C.

Then the solution is stirred at room temperature for 4 hours, washed with water, dried over sodium sulphate and the solvent is distilled off. 29.5 g. of N-(dichloroacetyl)-N-(n-butylglycine)-N'-phenyl amide are obtained; $n_D^{20}$=1.5256. Yield: 85%. Purity (determined by gas chromatographic analysis): 97.8%.

Analysis: Calculated: N: 8.09%; Cl: 20.57%; Found: N: 7.82%; Cl: 20.52%.

The physical data of compounds of the formula I prepared according to the methods of Examples 1 to 3 are listed in Table I.

TABLE I

| | Substituents | | | Physical constants | |
|---|---|---|---|---|---|
| No. | $R_1$ | $R_2$ | $R_3$ | Melting point °C. | $n_D^{20}$ |
| 1. | 2. | 3. | 4. | 5. | 6. |
| 1 | phenyl- | ethyl- | methyl- | 99–100 | |
| 2 | phenyl- | ethyl- | ethyl- | 56–58 | |
| 3 | phenyl- | ethyl- | n-propyl- | 94–95.5 | |
| 4 | phenyl- | ethyl- | i-propyl- | 109–110.5 | |
| 5 | phenyl- | ethyl- | allyl- | 83–86 | |
| 6 | phenyl- | ethyl- | n-butyl- | | 1.5256 |
| 7 | phenyl- | ethyl- | s-butyl- | | 1.5373 |
| 8 | phenyl- | ethyl- | i-butyl- | 118–119.5 | |
| 9 | phenyl- | ethyl- | t-butyl- | 100–101 | |
| 10 | allyl- | allyl- | methyl- | 81–82.5 | |
| 11 | allyl- | allyl- | ethyl- | 87–89.5 | |
| 12 | allyl- | allyl- | allyl- | 50–51 | |
| 13 | ethyl- | ethyl- | allyl- | 93–95.5 | |
| 14 | i-butyl- | i-butyl- | ethyl- | 75–76.5 | |
| 15 | methyl- | methyl- | n-propyl- | 76–79 | |
| 16 | methyl- | methyl- | i-propyl- | 98.5–100 | |
| 17 | methyl- | methyl- | allyl- | 105–112 | |
| 18 | methyl- | methyl- | ethyl- | 101.5–103 | |
| 19 | ethyl- | ethyl- | n-propyl- | 49–52 | |
| 20 | ethyl- | ethyl- | i-propyl- | 89–92 | |
| 21 | ethyl- | ethyl- | ethyl- | 112–113.5 | |
| 22 | cyclohexyl- | ethyl- | ethyl- | 86–88.5 | |
| 23 | phenyl- | hydrogen | ethyl- | 128.5–131 | |
| 24 | allyl- | hydrogen | allyl- | | 1.5250 |
| 25 | n-propyl- | n-propyl- | allyl- | 52–54 | |
| 26 | cyclohexyl- | hydrogen | allyl- | | 1.5198 |
| 27 | phenyl- | hydrogen | allyl- | 109–11.5 | |
| 28 | 2,6-dimethylphenyl- | hydrogen | ethyl- | | 1.5290 |
| 29 | 2,6-diethylphenyl | hydrogen | ethyl- | | 1.5252 |
| 30 | hexamethylene- | | ethyl- | | 1.5229 |
| 31 | 3-chlorophenyl- | hydrogen | ethyl- | | 1.5317 |
| 32 | ethyl- | ethyl- | n-butyl- | 65–66 | |
| 33 | ethyl- | ethyl- | i-butyl- | 59.5–62.5 | |
| 34 | ethyl- | ethyl- | s-butyl- | 93–94 | |
| 35 | ethyl- | ethyl- | tert-butyl- | 128–129 | |
| 36 | phenyl- | methyl- | ethyl- | 62–66 | |
| 37 | phenyl- | methyl- | n-propyl- | 97–98.5 | |
| 38 | phenyl- | methyl- | allyl- | 102–103 | |
| 39 | phenyl- | i-propyl- | ethyl- | 85–86 | |
| 40 | phenyl- | i-propyl- | allyl- | 79–82 | |
| 41 | methyl- | hydrogen | methyl- | 36–40 | |
| 42 | ethyl | hydrogen | ethyl- | 79–82.5 | |
| 43 | n-propyl- | hydrogen | n-propyl- | | 1.5010 |
| 44 | i-propyl- | hydrogen | i-propyl- | 132–133 | |
| 45 | n-butyl- | hydrogen | n-butyl- | | 1.4950 |
| 46 | i-butyl- | hydrogen | i-butyl- | | 1.4880 |
| 47 | s-butyl- | hydrogen | s-butyl- | 73–76 | |
| 48 | benzyl- | hydrogen | benzyl- | 82–84 | |
| 49 | n-propyl- | n-propyl- | allyl- | | 1.5020 |
| 50 | phenyl- | methyl- | methyl- | 146–147.5 | |
| 51 | phenyl- | methyl- | i-propyl- | 101–102 | |
| 52 | 2,6-dimethylphenyl- | hydrogen | methyl- | 154–155 | |
| 53 | 2,6-dimethylphenyl- | hydrogen | allyl- | 190–192 | |
| 54 | 2,6-diethylphenyl- | hydrogen | methyl- | 158–160 | |
| 55 | 2,6-diethylphenyl- | hydrogen | allyl- | 118–121 | |
| 56 | allyl- | hydrogen | n-butyl- | 54–56 | |
| 57 | allyl- | hydrogen | i-butyl- | 60–63 | |
| 58 | allyl- | hydrogen | i-propyl- | 61–62.5 | |
| 59 | allyl- | hydrogen | n-propyl- | | 1.5112 |
| 60 | allyl- | hydrogen | ethyl- | 80–83 | |

The herbicide compositions according to the invention can be used in the treatment of cultivated plants in the form of e.g. emulsifiable concentrates, wettable powders, granules, aqueous or oily suspensions. The preparation of the compositions are illustrated by the following, non-limiting examples.

EXAMPLE 4

50 parts by weight of compound 5 of Table I are homogenized with 21 parts by weight of artificial amorf silicic acid grist (Zeolex 444), 21 parts by weight of mineral siliceous earth carrier, 2 parts by weight of sodium alkylsuphonate (Netzer IS) wetting agent, 3 parts by weight of cresol-formaldehyde condensate (Hoe S 1494) and 3 parts by weight of sodium ligninsulphonate dispersing agent.

The mixture is ground into fine particles in an Alpine 100 LV mill of ultraplex type.

A wettable powder composition of 50% by weight of active ingredient content is obtained.

Floatability (after half an hour): 81%.

Wet sieve residue (on a sieve of 50μ): 1.65% by weight.

EXAMPLE 5

80 parts by weight of compound 8 of Table I, 12 parts by weight of Zeolex 444, 4 parts by weight of sodium oleoyl-methyltauride (Arkopon T) and 4 parts by weight of calcium ligninsulphonate dispersing agent are homogenized, then the mixture is grinded into fine particles in an Alpine 63 C mill of contraplex type.

A wettable powder composition of 80% by weight of active ingredient content is obtained.

Floatability (after half an hour): 76.5%

Wet sieve residue (on a sieve of 50μ): 1.26% by weight.

EXAMPLE 6

0.01 parts by weight of compound 2 of Table I are dissolved in 10 parts by weight of dichloromethane, then the solution is sprayed under shaking onto 9.99 parts by weight of amorph silicic acid (Wersalon S) carrier and dried.

To this mixture 22 parts by weight of siliceous earth, 60 parts by weight of calcium carbonate, 2 parts by weight of sodium alkylsuphonate wetting agent, 3 parts by weight of cresol-formaldehyde condensate and 3 parts by weight of sodium ligninsulphonate dispersing agent are added. The mixture is grinded in a laboratory ball mill for one hour and homogenized. A wettable powder composition containing 0.01% by weight of active ingredient is obtained.

Floatability (after half an hour): 84.5%.

Sieve residue (on a sieve of 50μ): 0.76% by weight.

EXAMPLE 7

To a round-bottom flask equipped with a stirrer 25 parts by weight of compound 19 of Table I are charged, thereafter a mixture of 26 parts by weight of xylene, 26 parts by weight of dichloromethane and 13 parts by weight of dimethyl formamide and a mixture of 10 parts by weight of calcium dodecylbenzenesulphonate and alkylphenol polyglycolether emulsifier are added. The stirring is continued until the components are completely dissolved. The emulsifiable concentrate obtained contains 25% by weight of active ingredient.

Emulsion stability [in a concentration of 1%, in water/water hardness: 24 Clark°/]:

after 2 hours: minimal reversible change
after 24 hours: reversible sedimentation.

EXAMPLE 8

0.01 parts by weight of compound 4 of Table I are dissolved in a mixture of 25 parts by weight of dichloromethane and 66.99 parts by weight of xylene under stirring. Thereafter 8 parts by weight of an emulsifier containing calcium dodecylbeneze sulphonate and polyxyethylene alkylphenol are added, the solution is homogenized by a 15 minute stirring and filtered. An emulsifiable concentrate containing 0.01% by weight of active ingredient is obtained.

Emulsion stability:
after two hours: stable
after 24 hours: reversible sedimentation.

EXAMPLE 9

80 parts by weight of compound 7 of Table I, 13 parts by weight of xylene and 7 parts by weight of an emulsifier containing calcium dodecylbenzene sulphonate and polyoxyethylene alkylphenol are homogenized by a laboratoy stirrer for 15 minutes, then filtered.

The emulsifiable concentrate obtained contains 80% by weight of active ingredient.

Emulsion stability:
after 0.5 hour: stable
after 2 hours: minimal reversible sedimentation.

EXAMPLE 10

0.01 parts by weight of compound 20 of Table I, 29.99 parts by weight of artificial amorph silicic acid carrier, 61 parts by weight of water, 0.2 parts by weight of polysaccharide concentrating agent, 0.8 parts by weight of alkylpolysiloxane anti-foam agent, 8 parts by weight of a tenside mixture containing calcium dodecylbenzene sulphonate, polyoxyethylene and alkylphenol and polyoxyethylene triglicerid are charged into a laboratory pearl mill and 300 g. of glass pearls of from 1.0 to 1.5 mm diameter are added. The suspension is grinded for 1 hour at a speed of 775 revolution/minute. The pearls are separated from the product on a sieve. The aqueous suspension concentrate contains 0.01% by weight of active ingredient.

Density: 1.07 g/cm$^3$

Floatability [after 30 minutes, in water/water hardness: 24 Clark°/] 94.6%.

EXAMPLE 11

50 parts by weight of compound 18 of Table I, 46 parts by weight of water, 0.5 parts by weight of alkylpolysiloxane anti-foam agent and 5.5 parts by weight of an emulsifier containing calcium dodecylbenzene sulphonate and polyoxyethylene alkylphenol are charged into a laboratory pearl mill and 300 g. of glass pearls of a diameter of from 1.0 to 1.5 mm. are added. The suspension is grinded for 1 hour at a speed of 775 revolution/minute. Then the pearls are separated from the product on a sieve. The aqueous suspension concentrate obtained contains 50% by weight of active ingredient.

Density: 1.095 g/cm$^3$.

Floatability: 91.4%.

EXAMPLE 12

40 parts by weight of compound 16 of Table I, 56 parts by weight of technical vaseline oil and 6 parts by weight of an emulsifier containing calcium dodecylbenzene sulphonate and polyoxyethylene and alcohol are charged into a laboratory pearl mill of 0.5 l. and 300 g. of glass pearls of a diameter of from 1.0 to 1.5 mm. are added. The suspension is grinded for 1 hour at a speed of 775 revolution/minute, then the product is separated from the pearls on a sieve. The oily suspension concentrate obtained contains 40% by weight of active ingredient.

Density: 0.95 g/cm$^3$.

Floatability/3% concentration; after 3 minutes/: 96.5%.

EXAMPLE 13

0.01 parts by weight of compound 19 of Table I is dissolved in 10 parts by weight of dichloromethane. The solution is sprayed onto Fugrane (a granular carrier of organic origin, produced by a Hungarian firm) of a diameter of from 0.2 to 1.0 mm. under stirring. Then the formulation is dried, the solvent is removed. The granules obtained contain 0.01% by weight of active ingredient. Volume weight: 600 g. l.

EXAMPLE 14

50 parts by weight of compound 23 of Table I, previously grinded, are homogenized with 50 parts by weight of gipsum in a powder mixer, then a paste is made by adding 12 parts by weight of a 0.4% by weight methyl cellulose solution. The paste is added to 1000 parts by weight of paraffine containing 0.5 parts by weight of sorbitol monolaurate surfactant under constant stirring. Due to the stirring the paste falls into small round particles, thereafter solidifies. After 1 hour of stirring the granules are filtered off from the solution, washed with n-hexane and dried. The granulate obtained contains 50% by weight of active ingredient. Volume weight: 0.52 g./cm$^3$.

EXAMPLE 15

10 parts by weight of compound 11 of Table I are dissolved in a mixture of 20 parts by weight of xylene and 20 parts by weight of dichloromethane. The solution is sprayed onto 90 parts by weight of calcinated siliceous earth granulate carrier of a diameter of from 0.4 to 1.0 mm. under vibration stirring, thereafter the solvent is removed at 40° C. in a vacuum drying oven. The granulate obtained contains 10% by weight of active ingredient. Volume weight: 0.56 g./cm$^3$.

EXAMPLE 16

0.5 parts by weight of compound 27 of Table I are dissolved in a mixture of 8 parts by weight of xylene and 3.5 parts by weight of dichloromethane. Thereafter 80 parts by weight of EPTC [N,N-di(n-propyl)-S-ethyl thiolcarbamate] and 8 parts by weight of an emulsifier containing calcium dodecylbenzene sulphonate and alkylphenol polyglycolether are added. The mixture is homogenized for 15 minutes, then filtered. The emulsifiable concentrate obtained contains altogether 80.5% by weight of active ingredient.

Emulsion stability:
after 2 hours: stable
after 24 hours: minimal reversible change

EXAMPLE 17

2 parts by weight of compound 13 of Table I are dissolved in a mixture of 7 parts by weight of xylene and 7 parts by weight of dimethyl formamide. Then 78 parts by weight of Butilate [N,N-diisobutyl-S-ethyl thiolcarbamate] and 6 parts by weight of an emulsifier mixture containing calcium dodecylbenzene sulphonate and alkylphenol polyglycolether are added, thereafter the mixture is homogenized for 20 minutes and filtered. The emulsifiable concentrate obtained contains altogether 80% by weight of active ingredient.

Emulsion stability:
after 2 hours: stable
after 24 hours: slight reversible sedimentation.

EXAMPLE 18

20 parts by weight of compound 10 of Table I are dissolved in a mixture of 6 parts by weight of xylene and 6 parts by weight of an isoformic solvent. Thereafter 60 parts by weight of Vernolate [N,N-di(n-propyl)-S-/n-propyl/thiocarbamate] and 8 parts by weight of an emulsifier mixture containing calcium dodecylbenzene sulphonate and alkylphenol polyglycolether are added. After homogenization the solution is filtered. The emulsifiabel concentrate obtained contains altogether 80% by weight of active ingredient.

Emulsion stability:
after 2 hours: stable
after 24 hours: slight reversible change.

EXAMPLE 19

5 parts by weight of Alachlor [2',6'-diethyl-N-(methoxyethyl)chloroacetanilide] and 0.8 parts by weight of compound 9 of Table I are dissolved in 10 parts by weight of dichloromethane. The solution is sprayed into 24.2 parts by weight of amorphous siliceous earth carrier under stirring, then the solvent is evaporated at a temperature of 30°–40° C. in a fluid dryer. Then 60 parts by weight of siliceous earth carrier, 3 parts by weight of sodium alkylsulphonate wetting agent, 3 parts by weight of cresol-formaldehyde condensate and 4 parts by weight of sulfite liquor dispersing agent are added to the powder mixture. The mixture is grinded to fine particles by an Alpine 63 C miller of contraplex type.

The wettable powder composition obtained contains altogether 5.8% by weight of active ingredient.

Floatability [concentration: 1%; in water (water hardness 24 Clark°)]: 81.6%.

Sieve residue (325 mechanical sieve): 0.82% by weight.

EXAMPLE 20

0.4 parts by weight of compound 24 of Table I are dissolved in 13.6 parts by weight of kerosine, then 80 parts by weight of EPTC active ingredient and 6 parts by weight of an emulsifier mixture containing Evemul A and Evemul B are added. The mixture is homogenized by a laboratory stirrer for 15 minutes, then filtered. The emulsifiable concentrate obtained contains 80.4% by weight of active ingredient.

EXAMPLE 21

The procedure of Example 20 is followed except that 80 parts by weight of Vernolate are charged instead of 80 parts by weight of EPTC.

EXAMPLE 22

The procedure of Example 20 is followed except that 80 parts by weight of Butilate are charged instead of 80 parts by weight of EPTC.

EXAMPLE 23

0.9 part by weight of compound 24 of Table I are dissolved in 3.1 parts by weight of kerosine. Thereafter 90 parts by weight of EPTC active ingredient and 6 parts by weight of an emulsifier mixture containing Evemul A and Evemul B are added and the solution is homogenized by a 15 minute stirring, then filtered on a filter. The emulsifiable concentrate obtained contains 90.9% by weight of active ingredient.

EXAMPLE 24

The procedure of Example 23 is followed except that 90 parts by weight of Vernolate are charged instead of 90 parts by weight of EPTC.

EXAMPLE 25

The procedure of Example 23 is followed except that 90 parts by weight of Butilate are charged instead of 90 parts by weight of EPTC.

EXAMPLE 26

1.6 parts by weight of compound 24 of Table I are dissolved in 12.4 parts by weight of xylene. Thereafter 80 parts by weight of EPTC active ingredient and 6 parts by weight of an emulsifier mixture containing Evemul A and Evemul B are added, the solution is stirred for 15 minutes, then filtered. The emulsifiable concentrate contains 81.6% by weight of active ingredients.

EXAMPLE 27

The procedure of Example 26 is followed except that 80 parts by weight of Vernolate are used instead of 80 parts by weight of EPTC.

EXAMPLE 28

The procedure of Example 26 is followed except that 80 parts by weight of Butilate are charged instead of 80 parts by weight of EPTC.

EXAMPLE 29

3 parts by weight of compound 24 of Table I are dissolved in 16 parts by weight of xylene, thereafter 75 parts by weight of EPTC and 6 parts by weight of an emulsifier mixture containing Evemul A and Evemul B are added. The solution is homogenized for 15 to 20 minutes, then filtered.

The emulsifiable concentrate obtained contains 78% by wegiht of active ingredients.

EXAMPLE 30

The procedure of Example 29 is followed except that 75 parts by weight of Vernolate are used instead of 75 parts by weight of EPTC.

EXAMPLE 31

The procedure of Example 29 is followed except that 75 parts by weight of Butilate are charged instead of 75 parts by weight of EPTC.

EXAMPLE 32

6 parts by weight of compound 24 of Table I are dissolved in a mixture of 6.5 parts by weight of xylene and 6.5 parts by weight of methylene chloride. Thereafter 75 parts by weight of EPTC and 6 parts by weight of an emulsifier mixture containing Evemul A and Evemul B are added under stirring. The solution is homogenized by stirring, then filtered.

The emulsifiable concentrate obtained contains 81 parts by weight of active ingredients.

EXAMPLE 33

The procedure of Example 32 is followed except that 75 parts by weight of Vernolate are charged instead of 75 parts by weight of EPTC.

EXAMPLE 34

The procedure of Example 32 is followed except that 75 parts by weight of Butilate are charged instead of 75 parts by weight of EPTC.

EXAMPLE 35

11.2 parts by weight of compound 24 Table I are dissolved in a mixture of 5.4 parts by weight of xylene and 5.4 parts by weight of methylene chloride. Thereafter 70 parts by weight of EPTC active ingredient and 8 parts by weight of an emulsifier mixture containing Evemul A and Evemul B are added. The solution is homogenized by a 15 minute stirring, then filtered.

The emulsifiable concentrate obtained contains 81.2% by weight of active ingredients.

EXAMPLE 36

The procedure of Example 35 is followed except that 70 parts by weight of Vernolate are used instead of 70 parts by weight of EPTC.

EXAMPLE 37

The procedure of Example 35 is followed except that 70 parts by weight of Butilate are charged instead of 70 parts by weight of EPTC.

EXAMPLE 38

19.2 parts by weight of compound 24 of Table I are dissolved in a mixture of 6.4 parts by weight of xylene and 6.4 parts by weight of the solvent soform. Thereafter 60 parts by weight of EPTC active ingredient and 8 parts by weight of an emulsifier mixture containing Evemul A and Evemul B are added under stirring. The solution is homogenized by a further 15 minute stirring, then filtered.

The emulsifiable concentrate obtained contains 79.2% by weight of active ingredients.

EXAMPLE 39

The procedure of Example 38 is followed except that 60 parts by weight of Vernolate are charged instead of 60 parts by weight of EPTC.

EXAMPLE 40

The procedure of Example 38 is followed except that 60 parts by weight of Butilate are charged instead of 60 parts by weight of EPTC.

EXAMPLE 41

25.6 parts by weight of compound 24 of Table I are dissolved in a mixture of 14.4 parts by weight of xylene and 10 parts by weight of dimethyl formamide. Thereafter 40 parts by weight of EPTC active ingredient and 10 parts by weight of an emulsifier mixture containing Evemul A and Evemul B are added. The solution is homogenized by stirring, then filtered.

The emulsifiable concentrate obtained contains 65.6% by weight of active ingredients.

EXAMPLE 42

The procedure of Example 41 is followed except that 40 parts by weight of Vernolate are charged instead of 40 parts by weight of EPTC.

EXAMPLE 43

The procedure of Example 41 is followed except that 40 parts by weight of Butilate are charged instead of 40 parts by weight of EPTC.

Evemul A used as an emulsifier in the above Examples is a mixture of alkylpolyglycol ethers and alkylaryl sulphonates while Evemul B is a mixture of alkylarly polyglycol ethers and alkylaryl sulphonates.

EXAMPLE 44

50 parts by weight of Alachlor and 0.25 parts by weight of compound 24 of Table I are dissolved in a mixture of 22 parts by weight of xylene and 21.75 parts by weight of dichloromethane, thereafter 6 parts by weight of an emulsifier mixture containing calcium alkylaryl sulphonate and a fatty acid polyglycol ester are added. The mixture is homgenized by stirring, then filtered.

An emulsifiable concentrate containing 50.25% by weight of active ingredients is obtained.

EXAMPLE 45

21.75 parts by weight of xylene and 21.75 parts by weight of dichloromethane are mixed, then 50 parts by weight of Alachlor and 0.5 parts by weight of compound 24 of Table I are dissolved in the solvent mixture. Then 6 parts by weight of an emulsifier mixture containing calcium alkylaryl sulphonate and a fatty acid polyglycol ester are added.

The emulsifiable concentrate obtained contains 50.5% by weight of active ingredients.

EXAMPLE 46

To 50 parts by weight of Alachlor 1 part by weight of compound 24 of Table I is charged, then the mixture is dissolved in a solvent mixture containing 21.5 parts by weight of xylene and 21.5 parts by weight of dichloromethane.

Then 6 parts by weight of an emulsifier mixture containing calcium alkylaryl sulphonate and a fatty acid polyglycol ester are added, the solution is homogenized and filtered.

The emulsifiable concentrate obtained contains 51% by weight of active ingredients.

EXAMPLE 47

50 parts by weight of Alachlor and 2 parts by weight of compound 24 of Table I are mixed, then the mixture is dissolved in a solvent mixture containing 20 parts by weight of xylene and 20 parts by weight of dichloromethane. Thereafter 8 parts by weight of an emulsifier mixture containing calcium alkylaryl sulphonate and fatty acid polyglycol ester are added. The solution is filtered after homogenization.

The emulsifiable concentrate obtained contains 52% by weight of active ingredients.

EXAMPLE 48

46.3 parts by weight of Alachlor and 3.7 parts by weight of compound 24 of Table I are dissolved in a mixture of 19 parts by weight of xylene, 19 parts by weight of dichloromethane and 4 parts by weight of dimethyl formamide. Thereafter 8 parts by weight of an emulsifier mixture containing calcium alkylaryl sulphonate and a fatty acid polyglycol ester are added under stirring. The solution is homogenized by further stirring, then filtered.

The emulsifiable concentrate obtained contains 50% by weight of active ingredients.

EXAMPLE 49

44 parts by weight of Alachlor, 7 parts by weight of compound 24 of Table I, a mixture of 18 parts by weight of xylene, 18 parts by weight of dichloromethane and 5 parts by weight of dimethyl formamide, further 8 parts by weight of an emulsifier mixture containing calcium alkylaryl sulphonate and a fatty acid polyglycol ester are homogenized by stirring. Finally the solution is filtered.

The emulsifiable concentrate obtained contains 51% by weight of active ingredients.

EXAMPLE 50

In a solvent mixture containing 18 parts by weight of xylene, 18 parts by weight of dichloromethane and 6 parts by weight dimethyl formamide 38 parts by weight of Alachlor and 12 parts by weight of compound 24 of Table I are dissolved. Thereafter 8 parts by weight of an emulsifier mixture containing calcium alkylaryl sulphonate and a fatty acid polyglycol ester are added.

The emulsifiable concentrate obtained contains 50% by weight of active ingredients.

EXAMPLE 51

30.5 parts by weight of Alachlor and 19.5 parts by weight of compound 24 of Table I are dissolved in a solvent mixture containing 16 parts by weight of xylene, 16 parts by weight of dichloromethane and 8 parts by weight of dimethyl formamide. The solution is stirred and 10 parts by weight of an emulsifier mixture containing calcium alkylarly sulphonate and a fatty acid polyglycol ester are added. The solution is homogenized by a further 15–20 minute stirring, then filtered.

The emulsifiable concentrate obtained contains 50% by weight of active ingredients.

The compositions of the wettable powder formulations (WP) prepared similarly to the method described in Example 4, by using the compounds of the formula I are listed in Table II.

TABLE II

| No. of the compound according to Table I | compound according to Table I | Zeolex 444 | mineral siliceous earth | Netzer IS | Hoe S 1494 | Sodium ligninsulphonate | The formulation |
|---|---|---|---|---|---|---|---|
| 1 | 2 | 3 | 4 | 5 | 6 | 7 | 8 |
| 1 | 0.1 | 20 | 72.4 | 1.5 | 3 | 3 | 0.1 WP |
| 2 | 10 | 30 | 52.5 | 1.5 | 3 | 3 | 10 WP |
| 3 | 80 | 10 | — | 2 | 4 | 4 | 80 WP |
| 4 | 30 | 30 | 30 | 2 | 4 | 4 | 30 WP |
| 5 | 20 | 72 | — | 2 | 3 | 3 | 20 WP |

TABLE II-continued

| No. of the compound according to Table I 1 | compound according to Table I 2 | Zeolex 444 3 | mineral siliceous earth 4 | Netzer IS 5 | Hoe S 1494 6 | Sodium ligninsulphonate 7 | The formulation 8 |
|---|---|---|---|---|---|---|---|
| 8 | 80 | 11 | — | 2 | 4 | 3 | 80 WP |
| 9 | 60 | 10 | 22.5 | 1.5 | 3 | 3 | 60 WP |
| 10 | 25 | 35 | 32 | 2 | 3 | 3 | 25 WP |
| 11 | 20 | 42 | 34 | 1.5 | 4 | 2.5 | 20 WP |
| 12 | 5 | 86 | — | 2 | 4 | 3 | 5 WP |
| 13 | 50 | 25 | 16 | 2 | 4 | 3 | 50 WP |
| 14 | 40 | 25 | 25 | 2 | 3 | 4 | 40 WP |
| 15 | 40 | 25 | 26 | 2 | 3 | 4 | 40 WP |
| 16 | 70 | 20 | 3 | 2 | 4 | 2 | 70 WP |
| 17 | 70 | 13 | 10 | 1 | 4 | 1 | 70 WP |
| 18 | 80 | 11.5 | — | 2 | 4 | 3 | 80 WP |
| 20 | 70 | 22.5 | — | 1.5 | 3 | 3 | 70 WP |
| 21 | 75 | 13 | 3 | 1.5 | 4 | 3 | 75 WP |
| 22 | 60 | 10 | 20 | 2 | 4 | 4 | 60 WP |
| 23 | 80 | 4 | — | 2 | 3 | 4 | 80 WP |
| 27 | 60 | 15 | 16 | 2 | 3 | 4 | 60 WP |
| 28 | 80 | 13.5 | — | 2 | 3 | 2.5 | 80 WP |
| 29 | 80 | 11 | — | 1.5 | 4 | 3 | 80 WP |
| 30 | 50 | 25 | 16 | 2 | 4 | 2 | 50 WP |
| 31 | 80 | 13 | — | 3 | 3 | 2 | 80 WP |
| 34 | 70 | 12 | 10 | 2 | 3 | 3 | 70 WP |
| 35 | 80 | 12 | — | 2 | 3 | 3 | 80 WP |
| 36 | 60 | 17 | 15 | 2 | 3 | 4 | 60 WP |
| 37 | 60 | 18 | 14 | 1 | 4 | 3 | 60 WP |
| 38 | 70 | 11 | 11 | 1 | 3 | 3 | 70 WP |
| 39 | 10 | 65 | 16 | 2 | 3 | 4 | 10 WP |
| 40 | 10 | 70 | 22 | 1 | 3 | 4 | 10 WP |
| 42 | 10 | 72 | 14 | 2 | 3 | 3 | 10 WP |
| 44 | 0.5 | 30 | — | 1 | 3 | 4 | 0.5 WP |
| 47 | 1.5 | 60 | 31 | 1.5 | 3 | 3 | 1.5 WP |
| 48 | 10 | 53 | 35 | 1 | 3 | 4 | 10 WP |
| 49 | 10 | 85 | — | 2 | 4 | 3 | 10 WP |
| 50 | 40 | 43 | — | 2 | 4 | 3 | 40 WP |
| 52 | 20 | 40 | 32 | 1 | 4 | 3 | 20 WP |
| 53 | 20 | 43 | 29 | 1 | 3 | 4 | 20 WP |
| 54 | 10 | 54 | 18 | 2 | 3 | 3 | 10 WP |
| 55 | 30 | 28 | 30 | 1 | 3 | 4 | 30 WP |
| 56 | 40 | 34 | 16 | 2 | 4 | 4 | 40 WP |
| 57 | 10 | 46 | 35 | 2 | 4 | 3 | 10 WP |
| 58 | 10 | 42 | 40 | 1 | 3 | 4 | 10 WP |
| 60 | 30 | 53 | 9 | 2 | 3 | 3 | 30 WP |

The compositions of the emulsifiable concentrate formulations (EP) prepared similarly to the method described in Example 7 by using the compounds of general formula I as active ingredients are listed in Table III.

TABLE III

| No. of the compound according to Table I 1 | Compound according to Table I 2 | Xylene 3 | Dichloromethane 4 | Dimethylformamide 5 | Tensiofix AS 6 | Tensiofix IS 7 | The formulation 8 |
|---|---|---|---|---|---|---|---|
| 6 | 80 | 7 | 7 | — | 3 | 3 | 80 EC |
| 7 | 10 | 40 | 40 | — | 5 | 5 | 10 EC |
| 19 | 20 | 35 | 35 | — | 5 | 5 | 20 EC |
| 24 | 50 | 15 | 15 | 10 | 5 | 5 | 50 EC |
| 25 | 40 | 20 | 20 | 10 | 5 | 5 | 40 EC |
| 26 | 80 | 5 | 5 | — | 5 | 5 | 80 EC |
| 32 | 30 | 25 | 25 | 10 | 5 | 5 | 30 EC |
| 33 | 20 | 30 | 30 | 10 | 5 | 5 | 20 EC |
| 36 | 0.1 | 45 | 44.9 | — | 5 | 5 | 0.1 EC |
| 41 | 10 | 40 | 40 | — | 5 | 5 | 10 EC |
| 45 | 70 | 10 | 10 | 2 | 4 | 4 | 70 EC |
| 46 | 60 | 20 | 12 | — | 4 | 4 | 60 EC |
| 49 | 20 | 50 | 21 | — | 4 | 5 | 20 EC |
| 51 | 0.1 | 50 | 41.9 | — | 4 | 4 | 0.1 EC |
| 59 | 10 | 30 | 30 | 20 | 5 | 5 | 10 EC |

EXAMPLE 52

25 parts by weight of compound 24 of Table I are dissolved in 64 parts by weight of kerosine. Then 5 parts by weight of EPTC active ingredient 6 parts by weight of an emulsifier mixture containing Evemul A and Evemul B are added, the solution is homogenized by a 15 minute stirring, finally filtered.

The emulsifiable concentrate obtained contains 30% by weight of active ingredients.

EXAMPLE 53

0.4 parts by weight of compound 7 of Table I are dissolved in 4.6 parts by weight of xylene and 90 parts by weight of EPTC active ingredient, then 6 parts by weight of an emulsifier mixture containing Evemul A and Evemul B are added under stirring. After a 15-20 minute homogenization the solution is filtered.

The emulsifiable concentrate obtained contains 5% by weight of active ingredients.

EXAMPLE 54

0.5 parts by weight of compound 51 of Table I are dissolved in a solvent mixture containing 62 parts by weight of xylene and 26 parts by weight of dichloromethane. Thereafter 5 parts by weight of Ethiolate active ingredient /N,N-diethyl-S-ethyl thiolcabamate/ and 4 parts by weight of Tensiofix AS and 2 parts by weight of Tensiofix IS emulsifiers are added under stirring. The solution is homogenized by a laboratory stirrer for 15 minutes, then filtered.

The emulsifiable concentrate obtained contains 5.5% by weight of active ingredients.

EXAMPLE 55

0.4 parts by weight of compound 59 of Table I are dissolved in a mixture containing 2 parts by weight of xylene and 1.6 parts by weight of dichloro methane. The solution obtained is stirred while 90 parts by weight of Ethiolate active ingredient, 3 parts by weight of Tensiofix AS and 3 parts by weight of Tensiofix IS emulsifiers are added. After a homogenization of 15 minutes the solvent is filtered.

The emulsifiable concentrate obtained contains 90.4% by weight of active ingredients.

EXAMPLE 56

To 5 parts by weight of Alachlor active ingredient 32 parts by weight of compound 46 of Table I are added, thereafter the mixture is dissolved in a solvent mixture containing 25 parts by weight of xylene, 20 parts by weight of dichloromethane and 15 parts by weight of dimethyl formamide. Thereafter an emulsifier mixture containing 6.5 parts by weight of Emulsogen IP and 1.5 parts by weight of Emulsogen EL are added, then the solution is homogenized and filtered.

The emulsifiable concentrate obtained contains 37% by weight of active ingredients.

EXAMPLE 57

65 parts by weight of Acetochlor [2-chloro-2-methyl-6′-ethyl-N-(ethyoxymethyl)acetanilide] active ingredient and 0.2 parts by weight of compound 57 of Table I are dissolved in a solvent mixture containing 22 parts by weight of xylene and 11 parts by weight of dimethyl formamide. Thereafter an emulsifier mixture containing 4.5 parts by weight of Emulsogen IP and 3.5 parts by weight of Emulsogen EL are added, then the solution is homogenized for 15 minutes and filtered.

The emulsifiable concentrate obtained contains 65.2% by weight of active ingredients.

EXAMPLE 58

To 5 parts by weight of Acetochlor and 32 parts by weight of compound 33 of Table I are added, thereafter they are dissolved in a solvent mixture containing 20 parts by weight of xylene, 15 parts by weight of dichloromethane and 10 parts by weight of dimethyl formamide. Thereafter an emulsifier concentrate containing 6 parts by weight of Emulsogen IP and 2 parts by weight of Emulsogen EL is added under stirring. The solution is homogenized, then filtered.

The emulsifiable concentrate obtained contains 37% by weight of active ingredients.

Emulsogen EL: oxyethylated castor oil
Emulsogen IP: alkylphenol polyethyleneglycol ether
Both of them are produced by Hoechst.

In the course of our experiments it was found that compounds of the formula I significantly reduced the well-known damaging effect of the thiolcarbamate and acetanilide herbicides of the formulae III and IV on cultivated plants, especially on maize. In order to determine the relationship between the dose applied and the effect achieved, experiments were carried out by using the compound of the formula I. The experiments showed that the addition of the compound of the formula I as an antidote in an amount of 0.5 to 64% by weight based on the amount of the herbicide used in the practice, said amount being taken as 100%, significantly increased the measured or estimated efficiency with a probability level of 95%.

The biological experiments carried out by using the formulations according to the invention are shown by the following Examples.

EXAMPLE 59

The test series were carried out in pots of a surface of 1.13 dm$^2$ in four replicate.

Firsty 400 g. of air dry field soil/Arany-type impermeable number: 61; pH$_{H2O}$=7.5/ sieved on a sieve with holes of 2 mm, containing 1.4% of humus were charged to the pots, thereafter the seeds of the test plants were placed onto it. 15 seeds/pot of maize (Zea mays), variety MVTC-596 and 0.5 g/pot of green foxtail (Setaria viritus) were used. Then the seeds were covered by 200 g. of soil, and the soil was treated by spraying the formulations according to the invention.

Based on the surfaces of the pots the amounts of the compositions were calculated as 1/ha. In order to prepare the spray, 20-20 ml. of water were added to the compositions.

After the treatment with the formulations, a further 100 g. of soil were charged into the pots, thereafter the pots were irrigated with an amount of water corresponding to the 65% of the water capacity of the soil, and in the course of growing the same humidity of the soil was assured by daily irrigations. The plants were cultivated under light substituting HgMI/D 400 W lamps in a lighting cycle of 14 hours. The daily average temperature was 25° C.

(minimum: 23° C.: maximum: 27° C.).

In order to evaluate the results, plants untreated with herbicides were also grown as controls.

The efficiency of the compositions according to the invention was compared to that of the compositions containing N,N-diallyl-2,2-dichloroacetamide (R-25,788) as a known antidote.

The evaluation was carried out on the 14th day counted from the day of the treatment by measuring the lenght of the maize sprout and observing the changes on the exterior of the maize. The changes in the shapes were evaluated according to the following scale:
100% healthy, unharmed maize
87% mild twist and deformation of the leaf
75% medium twist of the stem, leaf deformation
50% complete deformation, the growth and the development of the plant stopped.

The green foxtail seeded as monocotyledonus weed was controlled in every treatment, therefore it can be established, that the antidote action of compounds of the formula I is not extended to that weed.

TABLE IV

Protecting effect of compounds of the formula I on maize (the compounds of the formula I were used together 5.6 l/ha. EPTC; the results are expressed in % based on the untreated plants.)

| | Maize | | | |
|---|---|---|---|---|
| | Sprout length, % Dose of the antidote | | Exterior Dose of the antidote | |
| Treatments | 8% | 16% | 8% | 16% |
| EPTC 72EC | 35 | | 50 | |
| EPTC + R25788 | 95 a,b | | 98 a,b | |
| EPTC + compound No. of Table I | | | | |
| 1 | 56 b | 78 b | 70 b | 80 b |
| 2 | 49 b | 69 b | 65 b | 80 b |
| 3 | 33 | 37 | 55 | 55 |
| 4 | 29 | 29 | 55 | 55 |
| 5 | 45 | 58 b | 65 b | 70 b |
| 6 | 29 | 36 | 50 | 50 |
| 7 | 31 | 24 | 55 | 50 |
| 8 | 29 | 29 | 50 | 55 |
| 9 | 31 | 29 | 50 | 55 |
| 10 | 38 | 53 b | 60 | 65 b |
| 11 | 39 | 48 | 55 | 60 |
| 12 | 34 | 66 b | 63 b | 50 |
| 13 | 85 b | 93 a,b | 85 b | 99 a,b |
| 14 | 33 | 48 | 55 | 65 b |
| 15 | 33 | 44 | 50 | 57 |
| 16 | 27 | 30 | 52 | 53 |
| 17 | 37 | 32 | 55 | 80 b |
| 18 | 32 | 40 | 55 | 54 |
| 19 | 80 b | 80 b | 88 b | 88 a,b |
| 20 | 53 b | 58 b | 69 b | 55 |
| 21 | 25 | 36 | 53 | 65 b |
| 22 | 29 | 21 | 50 | 55 |
| 23 | 81 b | 83 b | 86 b | 92 a,b |
| 24 | 92 a,b | 100 a,b | 100 a,b | 99 a,b |
| 25 | 46 b | 65 b | 66 b | 76 b |
| 26 | 77 b | 94 a,b | 92 a,b | 99 a,b |
| 27 | 76 b | 92 a,b | 80 b | 99 a,b |
| 28 | 55 b | 54 b | 64 b | 69 b |
| 29 | 52 b | 60 b | 64 b | 64 b |
| 30 | 38 | 48 | 56 | 69 b |
| 31 | 42 | 38 | 64 b | 50 |
| 32 | 42 | 42 | 57 | 59 |
| 33 | 38 | 45 | 50 | 54 |
| 34 | 31 | 30 | 52 | 53 |
| 35 | 33 | 29 | 50 | 50 |
| 36 | 74 b | 77 b | 97 a,b | 99 a,b |
| 37 | 46 b | 62 b | 55 | 82 b |
| 38 | 60 b | 85 b | 90 a,b | 97 a,b |
| 39 | 31 | 28 | 50 | 50 |
| 40 | 32 | 31 | 50 | 50 |
| 41 | 87 b | 90 a,b | 100 a,b | 100 a,b |
| 42 | 83 b | 81 b | 100 a,b | 97 a,b |
| 43 | 88 b | 78 b | 98 a,b | 99 a,b |
| 44 | 47 b | 48 | 81 b | 87 a,b |
| 45 | 57 b | 65 b | 63 b | 55 |
| 47 | 55 b | 41 | 67 b | 57 |
| 48 | 34 | 40 | 50 | 50 |
| 49 | 43 b | 75 b | 59 | 94 a,b |
| 50 | 95 a,b | 96 a,b | 73 b | 79 b |
| 51 | 40 | 42 | 64 b | 50 |
| 52 | 41 | 45 | 61 | 55 |
| 53 | 35 | 41 | 50 | 57 |
| 54 | 30 | 35 | 58 | 51 |
| 55 | 31 | 38 | 62 b | 65 b |
| 56 | 35 | 36 | 60 | 55 |
| 57 | 32 | 38 | 64 b | 70 b |
| 58 | 56 b | 68 b | 65 b | 75 b |
| 59 | 94 a,b | 98 a,b | 80 b | 100 a,b |
| 60 | 95 a,b | 89 a,b | 88 a,b | 100 a,b |
| SD$_{5\%}$ | 10.6 | 13.3 | 11.7 | 13.9 | a - unsignificant difference compared with the untreated control with a probability level of 95%
b - significant difference compared to the plant treated with EPTC only with a probability level of 95%.

EXAMPLE 60

The effect of the different doses of compound 24 of Table I possessing antidote activity was tested. The test was carried out according to Example 59. The sprays were made from the compositions according to Examples 20 to 58.

For comparing the effect of the antidote, control maize plants were treated with EPTC, Vernolate, Butilate, Alachlor, Ethiolate, Acetochlor and with compositions containing these compounds as active ingredients and R-25,788 as antidote.

The maize sprout length and the change of the shape of the maize were measured and evaluated.

The results of the tests are listed in Tables V, VI, VII, VIII, IX and X.

TABLE V

Test of the sprout length and the change of the shape of maize. (The plants were treated with 5.6 l/ha. of EPTC and with different amounts of compound 24 of Table I and R-25,788 antidote; the results are expressed in % based on the untreated plants.)

| Antidote dose | | Sprout length of maize Antidotes | | | Exterior Antidotes | | |
|---|---|---|---|---|---|---|---|
| | | Comp. 24 of Table I | R-25,788 | Difference | Comp. 24 of Table I | R-25,788 | Difference |
| l/ha | % | a | b | a − b | a | b | a − b |
| 0.028 | 0.5 | 104 | 83 | +21 | 98 | 83 | +15 |
| 0.056 | 1.0 | 102 | 85 | +17 | 97 | 85 | +12 |
| 0.112 | 2.0 | 96 | 98 | −2 | 98 | 99 | −1 |
| 0.224 | 4.0 | 95 | 98 | −3 | 98 | 98 | 0 |
| 0.448 | 8.0 | 97 | 99 | −2 | 96 | 100 | −4 |
| 0.896 | 16.0 | 92 | 87 | +5 | 100 | 95 | +5 |
| 1.792 | 32.0 | 90 | 80 | +10 | 100 | 97 | +3 |
| 2.584 | 64.0 | 78 | 85 | −7 | 98 | 95 | +3 |

SD$_{5\%}$ = 16.3% between any two     SD$_{5\%}$ = 13.8% between any two

TABLE V-continued

Test of the sprout length and the change of the shape of maize. (The plants were treated with 5.6 l/ha. of EPTC and with different amounts of compound 24 of Table I and R-25,788 antidote; the results are expressed in % based on the untreated plants.)

| Antidote dose | | Sprout length of maize Antidotes | | | Exterior Antidotes | | |
|---|---|---|---|---|---|---|---|
| | | Comp. 24 of Table I | R-25,788 | Difference | Comp. 24 of Table I | R-25,788 | Difference |
| l/ha | % | a | b | a − b | a | b | a − b | combinations
Sprout length of maize treated with EPTC only, without any antidote: 52% combinations
Exterior of maize treated with EPTC only, without any antidote: 63%

TABLE VI

Test of the sprout length and exterior of maize (The plants were treated with 6.0 l/ha. of Butilate, with different amounts of compound 24 of Table I and R-25,788 antidote; the results are expressed in % based on the untreated plants.)

| Antidote dose | | Sprout length of maize Antidotes | | | Exterior Antidotes | | |
|---|---|---|---|---|---|---|---|
| | | Comp. 24 of Table I | R-25,788 | Difference | Comp. 24 of Table I | R-25,788 | Difference |
| l/ha | % | a | b | a − b | a | b | a − b |
| 0.03 | 0.5 | 105 | 88 | +17 | 97 | 85 | +12 |
| 0.06 | 1.0 | 102 | 81 | +21 | 97 | 84 | +13 |
| 0.12 | 2.0 | 96 | 90 | +6 | 98 | 97 | +1 |
| 0.24 | 4.0 | 96 | 98 | −2 | 98 | 100 | −2 |
| 0.48 | 8.0 | 93 | 94 | −2 | 99 | 99 | 0 |
| 0.96 | 16.0 | 81 | 90 | −9 | 94 | 99 | −5 |
| 1.92 | 32.0 | 82 | 74 | +8 | 99 | 92 | +7 |
| 3.84 | 64.0 | 82 | 72 | +10 | 94 | 98 | −4 |

$SD_{5\%}$ = 14.5 between any two combinations
Sprout length of maize treated with Butilate, without any antidote: 77.6%

$SD_{5\%}$ = 11.7% between any two combinations
Exterior of maize treated with Butilate, without any antidote: 85%

TABLE VII

Test of sprout length and exterior of maize (The plants were treated with 4.0 l/ha. of Vernolate, different doses of compound 24 of Table I and R-25,788 antidote; the results are expressed in % based on the untreated plants.)

| Antidote dose | | Sprout length of maize Antidotes | | | Exterior Antidotes | | |
|---|---|---|---|---|---|---|---|
| | | Comp. 24 of Table I | R-25,788 | Difference | Comp. 24 of Table I | R-25,788 | Difference |
| l/ha | % | a | b | a − b | a | b | a − b |
| 0.02 | 0.5 | 96 | 84 | +12 | 97 | 92 | +5 |
| 0.04 | 1.0 | 98 | 86 | +13 | 100 | 96 | +4 |
| 0.08 | 2.0 | 96 | 92 | +4 | 100 | 99 | +1 |
| 0.16 | 4.0 | 96 | 104 | −8 | 99 | 100 | −1 |
| 0.32 | 8.0 | 99 | 95 | +4 | 98 | 100 | −2 |
| 0.64 | 16.0 | 93 | 87 | +6 | 100 | 99 | +1 |
| 1.28 | 32.0 | 90 | 88 | +2 | 98 | 100 | −2 |
| 2.56 | 64.0 | 90 | 89 | +1 | 89 | 96 | −7 |

$SD_{5\%}$ = 11.5% between any two combinations
Sprout length of maize treated with Vernolate, without any antidote: 76%

$SD_{5\%}$ = 12.7% between any two combinations
Exterior of maize treated with Vernolate, without any antidote: 80%

TABLE VIII

Test of sprout length and exterior of maize (The plants were treated with 1.5 l/ha. of Alachlor, different doses of compound 24 of Table I and R-25,788 antidote; the results are expressed in % based on the untreated plants.)

| Antidote Dose | | Sprout length of maize Antidotes | | | Exterior Antidotes | | |
|---|---|---|---|---|---|---|---|
| | | Comp. 24 of Table I | R-25,788 | Difference | Comp. 24 of Table I | R-25,788 | Difference |
| l/ha | % | a | b | a − b | a | b | a − b |
| 0.008 | 0.5 | 91 | 81 | +10 | 97 | 87 | +10 |
| 0.015 | 1.0 | 98 | 87 | +11 | 98 | 84 | +14 |
| 0.030 | 2.0 | 104 | 105 | −1 | 98 | 97 | +1 |
| 0.060 | 4.0 | 97 | 107 | −10 | 99 | 94 | +5 |
| 0.120 | 8.0 | 97 | 114 | −17 | 99 | 100 | −1 |
| 0.240 | 16.0 | 96 | 100 | −4 | 100 | 97 | +3 |
| 0.480 | 32.0 | 93 | 97 | −4 | 100 | 100 | 0 |
| 0.960 | 64.0 | 86 | 97 | −11 | 100 | 99 | +1 |

$SD_{5\%}$ = 9.9% between any two $SD_{5\%}$ = 9.6% between any two

TABLE VIII-continued

Test of sprout length and exterior of maize (The plants were treated with 1.5 l/ha. of Alachlor, different doses of compound 24 of Table I and R-25,788 antidote; the results are expressed in % based on the untreated plants.)

| Antidote Dose | | Sprout length of maize Antidotes | | | Exterior Antidotes | | |
|---|---|---|---|---|---|---|---|
| | | Comp. 24 of Table I | R-25,788 | Difference | Comp. 24 of Table I | R-25,788 | Difference |
| l/ha | % | a | b | a − b | a | b | a − b | combinations
Sprout length of maize treated with
Alachlor, without any antidote: 81% combinations
Exterior of maize treated with
Alachlor, without any antidote: 80%

TABLE IX

Test of sprout length and exterior of maize (The plants were treated with 8.0 l/ha. of Ethiolate, different doses of compound 24 of Table I and R-25,788 antidote; the results are expressed in % based on the untreated plants.)

| Antidote Dose | | Sprout length of maize Antidotes | | | Exterior Antidotes | | |
|---|---|---|---|---|---|---|---|
| | | Comp. 24 of Table I | R-25,788 | Difference | Comp. 24 of Table I | R-25,788 | Difference |
| l/ha | % | a | b | a − b | a | b | a − b |
| 0.02 | 0.25 | 95 | 92 | +3 | 100 | 100 | 0 |
| 0.04 | 0.5 | 94 | 102 | −8 | 100 | 100 | 0 |
| 0.08 | 1.0 | 102 | 109 | −7 | 100 | 100 | 0 |
| 0.16 | 2.0 | 112 | 110 | +2 | 100 | 100 | 0 |
| 032 | 4.0 | 109 | 96 | +13 | 100 | 97 | +3 |
| 0.64 | 8.0 | 106 | 91 | +15 | 100 | 100 | 0 |
| 1.28 | 16.0 | 96 | 89 | +7 | 100 | 100 | 0 |
| 2.56 | 32.0 | 96 | 94 | +2 | 100 | 100 | 0 |
| 5.12 | 64.0 | 86 | 106 | −20 | 100 | 100 | 0 |

$SD_{5\%}$ = 11% between any two combinations
Sprout length of maize treated with
Ethiolate, without any antidote: 67%

$SD_{5\%}$ = 15% between any two combinations
Exterior of maize treated with
Ethiolate, without any antidote: 77%

TABLE X

Test of sprout length and exterior of maize (The plants were treated with 1.5 l/ha. of Acetochlor, different doses of compound 24 of Table I and R-25,788 antidote; the results are expressed in % based on the untreated plants.)

| Antidote Dose | | Sprout length of maize Antidotes | | | Exterior Antidotes | | |
|---|---|---|---|---|---|---|---|
| | | Comp. 24 of Table I | R-25,788 | Difference | Comp. 24 of Table I | R-25,788 | Difference |
| l/ha | % | a | b | a − b | a | b | a − b |
| 0.008 | 0.5 | 73 | 54 | +19 | 82 | 66 | +16 |
| 0.015 | 1.0 | 73 | 57 | +16 | 86 | 68 | +18 |
| 0.030 | 2.0 | 76 | 71 | +5 | 72 | 81 | −9 |
| 0.060 | 4.0 | 75 | 83 | −8 | 75 | 88 | −13 |
| 0.120 | 8.0 | 98 | 78 | +20 | 84 | 80 | +4 |
| 0.240 | 16.0 | 80 | 85 | −5 | 91 | 84 | +7 |
| 0.480 | 32.0 | 78 | 89 | −11 | 94 | 98 | −4 |
| 0.960 | 64.0 | 88 | 87 | +1 | 93 | 98 | −5 |

$SD_{5\%}$ = 9% between any two combinations
The sprout length of maize treated with
Acetochlor, without any antidote: 44%

$SD_{5\%}$ = 14% between any two combinations
Exterior of maize treated with
Acetochlor, without any antidote: 68%

The above Tables show that the antidotes according to the invention are advantageous in comparison to the known, widely used R-25,788 antidote when they are used in a dose of 0.5 to 2% calculated for the weight of the herbicidally active agent. If the antidote according the invention is used in higher concentrations, there could not be shown any difference between the effect of this antidote and R-25,788. A 4 to 16% dose of the antidotes assured healthy, symptomless maize.

The novel N- and optionally N'-substituted /N-dichloroacetyl/glycine amides of the invention enhance the selectivity of the thiolcarbamate and chloroacetanilide type herbicides, i.e. they eliminate the non-desired phytotoxic activity of the said compounds without decreasing their excellent herbicidal activity.

What we claim is:

1. An herbicide composition, which comprises an antidote of the Formula (I)

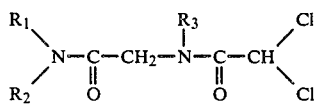

wherein
$R_1$ and $R_2$ are the same or different and represent hydrogen, alkyl, alkenyl, or together form a hexamethylene group; and
$R_3$ is alkyl or alkenyl; and an herbicidal compound of the Formula (III)

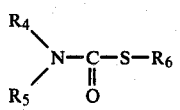

wherein $R_4$ and $R_5$ are the same or different and represent alkyl, cycloalkyl, or together form a hexamethylene group; and $R_6$ is alkyl; or an herbicidal compound of the formula (IV)

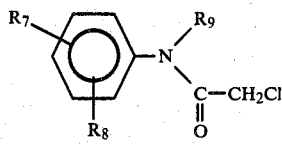

wherein $R_7$ and $R_8$ are the same or different and represent an alkyl group; and $R_9$ stands for alkyl, alkenyl, alkoxyalkyl, or pyrazolylalkyl; in association with at least one carrier or diluent.

2. An antidote composition which comprises N-(dichloroacetyl)-N-allylglycine-N'-allylamide together with at least one carrier or diluent.

3. The herbidical composition defined in claim 1 which comprises N-(dichloroacetyl)-N-allyglycine-N'-allylamide as the compound of the formula (I).

4. The herbicidal composition defined in claim 1 which comprises N-(dichloroacetyl)-N-allylglycine-N'-allylamide as the compound of the formula (I) and EPTC, Vernolate, Butilate or Ethiolate as the compound of the formula (III).

5. The herbicidal composition defined in claim 1 which comprises N-(dichloroacetyl)-N-allylglycine-N'-allylamide as the compound of the formula (I) and Alachlor or Acetochlor as the compound of the formula (IV).

6. A herbicide composition as claimed in claim 8 which comprises a compound of the formula I in 0.4 to 26% by weight, a compound of the formula III in 5 to 90% by weight in association with 5.5 to 60% by weight of carriers and/or diluents and/or excipients.

7. A herbicide composition as claimed in claim 1, wherein in the formula III $R_4$ and $R_5$ are the same or different and represent alkyl of 1 to 6 carbon atoms, cycloalkyl containing 5 to 6 carbon atoms or together form a hexamethylene group, $R_6$ stands for alkyl containing 1 to 5 carbon atoms.

8. A herbicide composition as claimed in claim 1 wherein in the formula IV $R_7$ and $R_8$ are the same or different and represent alkyl of 1 to 5 carbon atoms, $R_9$ stands for alkyl containing 1 to 5 carbon atoms, alkenyl containing 2 to 5 carbon atoms, alkoxyalkyl or pyrazolylalkyl.

9. A herbicide composition as claimed in claim 7, which comprises a compound of the formula I in 0.4 to 26% by weight, a compound of the formula III in 5 to 90% by weight in association with 5.5 to 60% by weight of carriers and/or diluents and/or excipients.

10. A herbicide composition as claimed in claim 1 which comprises 5 to 65% by weight of a compound of the formula IV, 0.2 to 32% by weight of a compound of the formula I in association with 10.5 to 60% by weight of carriers and/or diluents and/or excipients.

11. N-(dichloroacetyl)-N-allylglycine-N'-allylamide.

* * * * *